United States Patent
Kantam et al.

(10) Patent No.: US 6,245,950 B1
(45) Date of Patent: Jun. 12, 2001

(54) PROCESS FOR THE PREPARATION OF TETRABROMOBISPHENOL-A

(75) Inventors: Mannepalli Lakshmi Kantam; Katuri Jeevaratnam; Boyapati Manoranjan Choudary; Chinta Reddy Venkat Reddy; Kondapuram Vijaya Raghavan; Lanka Venkata Sivaji; Thumma Someshwar, all of Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/538,640

(22) Filed: Mar. 30, 2000

(51) Int. Cl.$^7$ .................................................. C07C 39/16
(52) U.S. Cl. ............................................................ 568/726
(58) Field of Search ................................................ 568/726

(56) References Cited

U.S. PATENT DOCUMENTS

| 3,546,302 | * | 12/1970 | Asadorian | 568/726 |
| 5,068,463 | | 11/1991 | Walter | 568/726 |
| 5,237,112 | * | 8/1993 | LaRose | 568/726 |

FOREIGN PATENT DOCUMENTS 62-48641 * 3/1987 (JP).

* cited by examiner

Primary Examiner—Michael L. Shippen
(74) Attorney, Agent, or Firm—Ladas & Parry

(57) ABSTRACT

The invention relates to a process for the preparation of high quality tetrabromobisphenol-A by reacting bisphenol-A with bromine and hydrogen peroxide as an oxidant in the presence of a heterogeneous catalyst in a biphase system consisting of water and water immiscible organic solvents.

10 Claims, No Drawings

PROCESS FOR THE PREPARATION OF TETRABROMOBISPHENOL-A

FIELD OF THE INVENTION

The present invention relates to an improved process for the preparation of Tetrabromobisphenol-A [4,4'-isopropylidene-bis-(2,6-dibromophenol)], a widely used flame retardant. More particularly, it relates to an eco-friendly process for the preparation of tetrabromobisphenol-A of a very high quality having low APHA color number and lower content of hydrolyzable bromine by bromination of bisphenol A using a heterogeneous catalyst, layered double hydroxides exchanged with tungstate.

BACKGROUND OF THE INVENTION

Tetrabromobisphenol-A hereafter referred to as TBBA is one of the most widely used and largest selling brominated flame-retardants in the world. It is used extensively to provide flame retardancy for styrenic thermoplastics and for some thermoset resins. The major markets for flame-retardants are the electrical, electronic appliances, automotives, textiles and furniture industry. The high quality TBBA is mandatory for flame-retardant polymers and plastics to be used in the electronics industry.

There are several known methods for the manufacture of TBBA, most of them covered in patents. Bromination of bisphenol A (BA) is an essential step in all the methods employed to obtain TBBA.

Bromination of BA is conventionally carried out using molecular bromine for the manufacture of TBBA. Since this involves electrophilic bromination, this method generates one mole of hydrogen bromide as an effluent per every mole of molecular bromine consumed. The generated hydrogen bromide on interaction with methanol gives methyl bromide, a widely used fumigant. Therefore, the earlier plants have integrated approach to fulfill the twin objectives of production of TBBA on interaction with molecular bromine and of methyl bromide from methanol employing generated hydrogen bromide. Methyl bromide, a fumigant, which is being banned, necessitates the development of an alternative process to use hydrogen bromide generated in the bromination of BA. In this connection, the function of haloperoxidase enzymes to oxidise the nucleophilic Br to the electrophilic $Br^+$, observed in nature, inspired us to explore the possibility of oxidising the nucleophile, Br, of the hydrogen bromide into the electrophilic bromine in order to use liberated HBr in the reaction of bromination of BA for the bromination of BA. Herein, we describe a heterogeneous catalyst, layered double hydroxides exchanged with tungstate that catalyses oxidative bromination in a selective manner. The low cost of the catalyst, reusability for several times and its ability to utilise the two atoms of the elemental bromine, raise the prospect of being successful in developing a clean and efficient industrial route to brominated chemicals and drugs.

Reference may be made to a U.S. Pat. No. 3,536,302, wherein TBBA is formed by reacting bisphenol-A and bromine in methanol. Thus, for the production of tetrabromobisphenol-A, equivalent amounts of HBr are generated. The HBr in turn reacts with the methanol solvent to produce the methyl bromide as a co-product. The drawbacks in the above process are the formation of methyl bromide, which is going to be a banned chemical and that the recovery and reuse of hydrogen bromide is cumbersome.

Reference may be made to a Japanese patent 77034620 B4 77/09/05 and U.S. Pat. Nos. 3,929,907; 4,180,684; 5,068,463, wherein the bisphenol-A is brominated in a biphase system comprising of water, water immiscible halogenated organic compound and an oxidant. The oxidant oxidizes the HBr to $Br_2$, which in turn is then available to brominate more bisphenol-A and its under-brominated species. The disadvantages of these processes are longer reaction times and the high expense of handling. In addition, the cooling of the solution to recover tetrabromobisphenol-A entails additional expenditure and process time.

Reference may be made to Japanese patent 1979-55538, May 2, 1979, wherein TBBA was prepared by the bromination of bisphenol-A in the presence of organic solvents and aqueous solutions and an improvement in the product separation was done by incorporating an active surface agent at the end of the reaction, to cause the separation of the emulsion into a distinct phase. The drawback in the above process is that the product is of inferior quality.

Reference may be made to U.S. Pat. Nos. 4,990,321; 5,008,469; 5,059,726, and 5,138,103 wherein bisphenol-A is brominated at a low temperature, 0° to 20° C., in the presence of a methanol solvent and a specified amount of water. The amount of water used, however, is not so large so as to cause the precipitation of the tetrabromobisphenol-A from the reaction mass. Additional water for that purpose is added at the end of the reaction. The drawbacks with these processes are that they use a fairly long aging or cooking period after the reactants have all been fed and require an additional process time for the final precipitation of tetrabromobisphenol-A via the last water addition.

Reference may be made to a U.S. Pat. No. 6,002,050 wherein bisphenol-A saturated with TBBA is brominated in the presence of water, water miscible solvent containing $H_2O_2$ and 1–20 wt. % of acid at a relatively high temperature. The drawbacks with this process are high temperature, long reaction times, presence of large amount of water and formation of small amounts of methyl bromide.

As long as there is a viable market for methyl bromide, the processes have been found to be commercially attractive. However, it is now being proposed, on an international level, that the use of methyl bromide as a fumigant be prohibited. Since the fumigant market is the main market for methyl bromide, a need is apparent for tetrabromobisphenol-A processes which do not co-produce a substantial amount of methyl bromide. This is a difficult task because, to be commercially successful, such processes will be required to economically produce tetrabromobisphenol-A without the benefit of the revenue realized from the sale of the co-product methyl bromide.

Obviously, different approaches have been employed to prepare TBBA. Our invention relates to the use of a heterogeneous catalyst, layered double hydroxides exchanged with tungstate for the preparation of TBBA.

OBJECTS OF THE INVENTION

The main object of the present invention is to provide an improved eco-friendly process for the preparation of TBBA of a very high quality which comprises reacting bisphenol-A with bromine and hydrogen peroxide as an oxidant in the presence of a heterogeneous catalyst, layered double hydroxides exchanged with tungstate in a biphase system consisting of water and water immiscible organic solvents at a temperature ranges between 20–75° C. for a period of 8–15 min under vigorous stirring and separating the organic layer from the reaction mixture to obtain the product by known methods which obviates the drawbacks as detailed above.

Another object of the present invention is the usage of non-corrosive and low cost heterogeneous catalyst selected from layered double hydroxides exchanged with tungstate.

It is another object of the invention to provide a process that is eco-friendly and simple.

It is another object of the invention to provide a process that is economical and is accomplished in a short time.

It is a further object of the invention to provide a process that results in high quality product.

Still another object of the present invention is the use of the recyclable catalyst.

Yet another object of the present invention is an additional step of bleaching of the final product carried out by sodium sulphite.

SUMMARY OF THE INVENTION

Accordingly, the present invention provides an improved process for the preparation of tetrabromobisphenol-A of a very high quality which comprises reacting bisphenol-A with bromine and hydrogen peroxide as an oxidant in presence of a heterogeneous catalyst in a biphase system consisting of water and water immiscible organic solvents at a temperature ranges between 20–75° C. for a period of 8–15 min under vigorous stirring and separating organic layer from the reaction mixture to obtain the product by known methods.

In an embodiment of the present invention, the heterogeneous catalyst used is selected from layered double hydroxides of the hydrotalcite family exchanged with tungstate.

In an embodiment of the present invention, bromine is added in a controlled manner during the period specified.

In an embodiment of the present invention, vigorous stirring is needed to mix the biphase system properly.

In yet another embodiment of the present invention, the catalyst introduced in the system is 2–5 ppm.

In still another embodiment of the present invention, water immiscible solvents such as n-pentane, n-hexane, n-octane, methylene chloride, dichloroethane, chlorobenzene and toluene are used.

In still another embodiment of the present invention, the reaction is effected at a temperature in the range of 20 to 75° for 8–10 min.

In still another embodiment of the present invention, the amount of hydrogen peroxide is 2.05 to 2.18 moles per mole of biphenol A.

In still another embodiment of the present invention, the amount of bromine is 2.05 to 2.1 moles per mole of bisphenol A.

In still another embodiment of the present invention, an additional step of bleaching the final product is carried out by sodium sulphite.

DETAILED DESCRIPTION OF THE INVENTION

The novelty of the invention lies in the use of heterogeneous catalyst for the first time for bromination of BA to obtain TBBA. The tungstate anion intercalated in the layered double hydroxide effectively catalyses the oxidation of Br to an electrophilic $Br^+$. These peroxy tungstate oxidises Br of HBr liberated during the reaction of $Br_2$ with BA to electrophilic $Br^+$ to facilitate the electrophilic substitution of BA with the second bromine atom of the bromine molecule. Since the heterogeneous catalyst is hydrophilic, it remains in the aqueous layer during separation of organic layer containing product from aqueous layer. The aqueous layer comprising of the catalyst is thus recycled for several times without any addition of fresh catalyst and recoursing filtration. Thus, the invention provides an economically viable process because the catalyst is reusable and sourced from cheaper raw materials.

SCIENTIFIC EXPLANATION

The catalytic cycle in the bromination of BA to TBBA involves the easy formation of peroxotungstate on interaction of tungstate with hydrogen peroxide. These peroxy species oxidises Br of HBr liberated during the reaction of $Br_2$ with BA to electrophilic $Br^+$ to facilitate the electrophilic substitution of BA with the second bromine atom of the bromine molecule. In summing up, tungstate acts as a catalyst in the oxidation of Br to $Br^+$. Controlled addition of bromine in the reaction flask is warranted to prevent the side reaction, decomposition of hydrogen peroxide The following examples are given by way of illustration of the present invention and therefore should not be construed to limit the scope of the present invention.

EXAMPLE 1

Catalyst Preparation a) Catalyst A: Ni—Al—Cl hydrotalcite exchanged with tungstate Ni—Al—Cl hydrotalcite (3:1) is prepared as follows: About 200 ml of decarbonated and deionised water was taken into a 1 liter four neck round bottomed flask and stirred at 25° C. with a magnetic stirrer under nitrogen flow. The mixture ($Al^{3+}$=0.05 mol/l), ($Ni^{2+}$=0.15 mol/l) of decarbonated solution of $AlCl_3.9H_2O$ (12.07 g), $NiCl_2.6H_2O$ (35.65 g) (obtained from M/S. Fluka, a Sigma Aldrich Company, Switzerland) and aqueous solution of sodium hydroxide (16 g, 0.2 mol/l) were added continuously dropwise from a burette, the pH of the reaction mixture being kept at 10.00–10.2 during the reaction. The precipitate obtained was filtered, washed with deionised and decarbonated water and dried at 70° C. for 15 h.

To reach anion exchange of degree of 12%, 1 g of Ni—Al—Cl hydrotalcite is stirred in 100 ml of aqueous 1.87 mM (0.616 g) sodium tungstate (obtained from M/S. Fluka, a Sigma Aldrich Company, Switzerland), at 293K for 24 h. The solid catalyst is filtered, washed with deionised and decarbonated water and lyophilized to dryness.

b) Catalyst B: Mg—Al—Cl Hydrotalcite Exchanged with Tungstate

Mg—Al—Cl hydrotalcite (3:1) is prepared as follows: About 200 ml of decarbonated and deionised water was taken into a 1 liter four neck round bottomed flask and stirred at 25° C. with a magnetic stirrer under nitrogen flow. The mixture ($Al^{3+}$=0.05 mol/l), ($Mg^{2+}$=0.15 mol/l) of decarbonated solution of $AlCl_3.9H_2O$ (12.07 g), $MgCl_2.6H_2O$ (30.49 g) (obtained from M/S. Fluka, a Sigma Aldrich Company, Switzerland) and aqueous solution of sodium hydroxide (16 g, 0.2 mol/l) were added continuously dropwise from a burette, the pH of the reaction mixture being kept at 10.00–10.2 during the reaction. The precipitate obtained was filtered, washed with deionised and decarbonated water and dried at 70° C. for 15 h.

To reach anion exchange of degree of 12%, 1 g of Mg—Al—Cl hydrotalcite is stirred in 100 ml of aqueous 1.87 mM (0.616 g) sodium tungstate (obtained from M/S. Fluka, Sigma Aldrich Company, Switzerland), at 293K for 24 h. The solid catalyst is filtered, washed with of deionised and decarbonated water and lyophilized to dryness.

EXAMPLE 2

100 g of bisphenol A is taken in a 2 liter round bottomed flask together with 600 ml of dichloroethane (DCE), 75 mg of catalyst A, 20 ml of water and 66.58 g of 49% hydrogen peroxide and thoroughly stirred. Then 147.7 g of bromine is added continuously over a period of 8–10 minutes using a pressure-equalising funnel. Bromine addition is executed at a controlled manner such that no bromine vapour escapes from the reflux condenser. The reaction mixture is stirred at the same temperature for 30 min. Stirring is terminated and the reaction mass is transferred and allowed to settle in a separating funnel at 60–65° C. Aqueous and organic layers are separated. The organic layer is fed to the same 2 liter flask and 15 g of sodium sulphite dissolved in 700 ml of water is added to the organic layer while stirring. The contents are heated in the Isomantle to recover DCE. As the DCE is being evaporated, the product separates from the organic layer as a solid. After the DCE recovery, the slurry is filtered to separate the solid product from the aqueous layer. The cake is reslurried with water, stirred for 10–15 min. and filtered. The cake is dried in a vacuum drier. The dried product is TBBA. The purity of the product in this case was 99.88% TBBA (as determined by HPLC) and the yield of the product was 95%.

EXAMPLE 3

100 g of bisphenol A is taken in a 2 liter round bottomed flask together with 600 ml of dichloroethane (DCE), 75 mg of catalyst B, 20 ml of water and 66.5 g of 49% hydrogen peroxide and thoroughly stirred. Then 147.7 g of bromine is added continuously over a period of 8–10 minutes using a pressure-equalising funnel. Bromine addition is executed at a controlled manner such that no bromine vapour escapes from the reflux condenser. The reaction mixture is stirred at the same temperature for 30 min. Stirring is terminated and the reaction mass is transferred and allowed to settle in a separating funnel at 60–65° C. Aqueous and organic layers are separated. The organic layer is fed to the same 2 liter flask and 15 g of sodium sulphite dissolved in 700 ml of water is added to the organic layer while stirring. The contents are heated in the Isomantle to recover the DCE. As the DCE is being evaporated, the product separates from the organic layer as a solid. After the DCE recovery, the slurry is filtered to separate the solid product from the aqueous layer. The cake is reslurried with water, stirred for 10–15 min. and filtered. The cake is dried in a vacuum drier. The dried product is TBBA. The purity of the product in this case was 99.72% TBBA (as determined by HPLC) and the yield of the product was 95%.

EXAMPLE 4

Recycle Experiment

The aqueous layer (65 ml) obtained in the example 2 was used with out any further addition of fresh catalyst for this recycle experiment.

100 g of bisphenol A is taken in a 2 liter round bottomed flask together with the aqueous layer (65 ml) obtained in example 2, 600 ml of dichloroethane (DCE) and 64 g of 49% hydrogen peroxide and thoroughly stirred. Then 147.7 g of bromine is added continuously over a period of 8–10 minutes using a pressure-equalising funnel. Bromine addition is executed at a controlled manner such that no bromine vapour escapes from the reflux condenser. The reaction mixture is stirred at the same temperature for 30 min. Stirring is terminated and the reaction mass is transferred and allowed to settle in a separating funnel at 60–65° C. Aqueous and organic layers are separated. The organic layer is fed to the same 2 liter flask and 15 g of sodium sulphite dissolved in 700 ml of water is added to the organic layer while stirring. The contents are heated in the Isomantle to recover DCE. As the DCE is being evaporated, the product separates from the organic layer as a solid. After the DCE recovery, the slurry is filtered to separate the solid product from the aqueous layer. The cake is reslurried with water, stirred for 10–15 min. and filtered. The cake is dried in a vacuum drier. The dried product is TBBA. The purity of the product in this case was 99.57% TBBA (as determined by HPLC) and the yield of the product was 96%.

TABLE 1

| | | | Tetrabromobisphenol-A | | | | |
|---|---|---|---|---|---|---|---|
| S. No. | Example[a] | Bisphenol-A (g) | Catalyst | Yield[b] (%) | Purity[c] | APHA[d] | Hydrolyzable Bromide (ppm) |
| 1 | 2 | 100 | A | 95 | 99.88 | 6 | 24 |
| 2 | 3 | 100 | B | 95 | 99.72 | 5 | 24 |
| 3 | 4 | 100 | A | 96 | 99.57 | 8 | 16 |

[a]As exemplified in the text.
[b]isolated yields.
[c]As determined by HPLC.
[d]APHA color number in 20% MeOH.

The main advantages of the present invention are:

1. The present process is eco-friendly and very simple.
2. The catalyst is cheap, non-corrosive, recyclable for several times and heterogeneous in nature.
3. Both the atoms of the elemental bromine are utilized with this heterogeneous catalyst.
4. The process is economical.
5. The process is accomplished in a short time.
6. The amount of effluents formed in this process is minimized because the catalyst, solvent and water are recovered/recycled and reused.
7. The process provides high quality of the product.

We claim:

1. A process for preparing tetrabromobisphenol-A comprising the steps of:

a) reacting bisphenol-A with hydrogen peroxide in the presence of a heterogeneous catalyst, wherein the heterogeneous catalyst is selected from double layered hydroxides exchanged with tungstate to form a reaction mixture;

b) stirring bromine into the reaction mixture;

c) allowing the reaction mixture to separate into an aqueous phase and an organic phase; and d) treating the organic phase with sodium sulphate to form tetrabromobisphenol-A.

2. A process as claimed in claim 1 wherein the heterogeneous catalyst introduced in the reaction mixture ranges between 2–5 ppm of the reaction mixture.

3. A process as claimed in claim 1 wherein the bromine used ranges between 2.05 to 2.1 moles per mole of bisphenol A.

4. A process as claimed in claim 1 wherein the hydrogen peroxide used ranges between 2.05 to 2.18 moles per mole of bisphenol A.

5. A process as claimed in claim 1 wherein the tetrabromobisphenol-A is bleached with sodium sulphite.

6. A process as claimed in claim 1, further comprising:

mixing the aqueous phase of step c) with Bisphenol-A, hydrogen peroxide, and bromine;

allowing the reaction mixture to separate into an aqueous phase and an organic phase;

treating the organic phase with sodium sulphate to form tetrabromobisphenol-A.

7. A process as claimed in claim 1, wherein the aqueous phase comprises water and water immiscible organic solvents.

8. A process as claimed in claim 7 wherein the water immiscible organic solvent is selected from the group consisting of n-pentane, n-hexane, n-octane, methylene chloride, dichloroethane, chlorobenzene and toluene.

9. A process as claimed in claim 1, wherein the heterogenous catalyst is selected from double layered hydroxides of the hydrotalcite family exchanged with tungstate.

10. A process as claimed in claim 1, wherein the stirring of bromine in step c) is carried out at a temperature in the range of 20 to 75° C. for a period of 8–15 min.

* * * * *